United States Patent
Min et al.

(10) Patent No.: US 7,440,804 B1
(45) Date of Patent: Oct. 21, 2008

(54) SYSTEM AND METHOD FOR MEASURING VENTRICULAR EVOKED RESPONSE USING AN IMPLANTABLE MEDICAL DEVICE

(75) Inventors: Xiaoyi Min, Thousand Oaks, CA (US); Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 521 days.

(21) Appl. No.: 11/025,220

(22) Filed: Dec. 28, 2004

(51) Int. Cl.
*A61N 1/378* (2006.01)
(52) U.S. Cl. ........................................ 607/28
(58) Field of Classification Search .................. 600/373, 600/374, 377, 393, 509; 607/4, 5, 6, 9, 11, 607/116, 122
See application file for complete search history.

(56) References Cited

U.S. PATENT DOCUMENTS

| | | | | |
|---|---|---|---|---|
| 4,228,803 A | * | 10/1980 | Rickards | 607/25 |
| 5,328,460 A | | 7/1994 | Lord et al. | 604/67 |
| 5,334,220 A | | 8/1994 | Sholder | 607/9 |
| 5,697,957 A | | 12/1997 | Noren et al. | 607/28 |
| 5,902,324 A | * | 5/1999 | Thompson et al. | 607/9 |
| 6,112,116 A | * | 8/2000 | Fischell et al. | 600/517 |
| 6,430,439 B1 | * | 8/2002 | Wentkowski et al. | 607/9 |
| 6,473,647 B1 | | 10/2002 | Bradley | 607/27 |
| 6,496,730 B1 | * | 12/2002 | Kleckner et al. | 607/9 |
| 6,512,952 B2 | | 1/2003 | Stahmann et al. | 607/9 |
| 6,622,045 B2 | | 9/2003 | Snell et al. | 607/30 |
| 6,628,988 B2 | | 9/2003 | Kramer et al. | 607/9 |
| 6,643,546 B2 | | 11/2003 | Mathis et al. | 607/9 |
| 6,645,153 B2 | | 11/2003 | Kroll et al. | 600/481 |
| 6,711,439 B1 | | 3/2004 | Bradley et al. | 607/9 |
| 7,072,715 B1 | * | 7/2006 | Bradley | 607/17 |
| 7,272,443 B2 | * | 9/2007 | Min et al. | 607/17 |
| 2004/0138716 A1 | | 7/2004 | Koh et al. | 607/17 |

* cited by examiner

*Primary Examiner*—Carl H. Layno
*Assistant Examiner*—Frances P Oropeza

(57) ABSTRACT

Techniques are provided for measuring ventricular evoked response within the heart of a patient during atrial fibrillation. An intrinsic ventricular depolarization (i.e. a QRS complex) is sensed within the right ventricle and then a pacing pulse is applied to the left ventricle prior to intrinsic depolarization thereof. In this manner, the left ventricle contracts solely in response to the pacing pulse and possible fusion between the pacing pulse and a conducted P-wave/A-pulse from the atria is avoided. The evoked response generated in the left ventricle is then measured by the pacemaker. The technique permits reliable detection of left ventricular evoked response, even during atrial fibrillation when atrial contractions are frequent and erratic, but the technique may also be employed during normal sinus rhythm. Features of the evoked response are analyzed to detect heart failure, evaluate its severity and track its progression. Appropriate therapy is then automatically delivered to the patient.

2 Claims, 10 Drawing Sheets

SYSTEM AND METHOD FOR MEASURING VENTRICULAR EVOKED RESPONSE USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for measuring ventricular evoked response for the purposes of tracking the progression of heart failure within a patient in which a medical device is implanted.

BACKGROUND

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and where increased discomfort is experienced with any physical activity.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing".

In view of the potential severity of heart failure, it is highly desirable to detect its onset within a patient and to track its progression or regression so that appropriate therapy can be provided. Many patients suffering heart failure already have pacemakers or ICDs implanted therein or are candidates for such devices. Accordingly, it is desirable to provide such devices with the capability to automatically detect and track heart failure and, heretofore, various techniques have been developed for monitoring physiological parameters associated with heart failure using implantable devices.

For example, U.S. Pat. No. 6,473,647 to Bradley, entitled "Implantable Cardiac Stimulation Device For and Method of Monitoring Progression or Regression of Heart Disease by Monitoring Evoked Response Features" sets forth techniques for tracking heart failure based upon changes in characteristics of the ventricular evoked response, i.e. based on changes within selected characteristics of the electrical depolarization profile generated during contraction of ventricular myocardial tissue in response to a pacing pulse of known amplitude. See also U.S. Pat. No. 6,711,439 to Bradley, et al., entitled "Evoked Response Variability as an Indicator of Autonomic Tone and Surrogate for Patient Condition."

FIG. 1 provides stylized representations of a ventricular evoked response profile triggered in response to a V-pulse for a healthy patient and one for a patient suffering symptoms of heart failure. Briefly, evoked response profile 10 for the healthy patient exhibits a larger positive amplitude 12, a larger negative amplitude 14, and a steeper positive slope 16 than corresponding features of the evoked response profile 18 of the heart failure patient. Accordingly, an analysis of changes in these features over time may be used to detect the onset of heart failure and track its progression. The particular manner by which changes in these and other characteristics of the evoked response are related to heart failure are discussed in greater detail below and are set forth in detail in the aforementioned patents to Bradley and Bradley, et al., which are incorporated fully by reference herein. For the purposes of FIG. 1, it is sufficient to note that the progression of heart failure within a patient may be tracked based upon an examination of changes in the ventricular evoked response profile, assuming that the profile can be reliably detected. Problems, however, can arise in the detection of the evoked response profile due to possible fusion of conducted P-waves or paced atrial beats (A-pulses) from the atria and ventricular pacing pulses. P-waves are electrical signals associated with intrinsic atrial contractions. A-pulses are artificial electrical pacing pulses applied to the atria. In either case, the electrical signals then conduct through atrioventricular (AV) conduction channels of the heart to the ventricles where they can trigger contraction of the ventricles.

FIGS. 2-4 illustrate problems that may arise in the detection of a ventricular evoked response profile due to fusion with conducted P-waves. Although not shown, similar problems arise due to conducted A-pulses. Referring first to FIG. 2, the figure illustrates an atrial intracardiac electrogram (A-IEGM) signal 20 and a corresponding ventricular IEGM (V-IEGM) signal 22 during a normal sinus rhythm. Note that the various features illustrated in FIG. 2, and within all other graphs of this patent application, are stylized representations of electrical signals, which are not intended to represent actual clinically-detected data. For clarity, various blanking intervals or refractory periods that may be employed by the pacemaker are not shown. In response to a P-wave detected within the A-IEGM, a ventricular pacing pulse (V-pulse) is delivered to the ventricles by the pacemaker subject to a programmed PV pacing delay value. The V-pulse triggers an evoked response, the profile of which may be measured within the V-IEGM for the purposes of tracking heart failure or for other reasons. The magnitude and shape of the evoked response depends on the magnitude and shape of the electrical simulation that triggers the evoked response and on the location within the ventricles in which the stimulation is applied. The magnitude and shape of the V-pulse is known. However, the V-pulse fuses with the conducted P-wave such that the magnitude and shape of the electrical stimulation delivered to the ventricles is different from that of the V-pulse by itself. (Phantom lines illustrate the conduction of the P-wave from the atria to the ventricles.) In this regard, the P-wave propagates through AV conduction pathways from the atria to the ventricles where, in the example of FIG. 2, it merges with or fuses with the V-pulse applied by the pacemaker to ventricles. Moreover, the ventricles now contract in response to electrical signals emanating from different locations, i.e. from the ventricular pacing electrode and from the AV conduction channels through which the P-wave propagates. As a result, the magnitude and shape of the evoked response measured with the ventricles differs from that of the "true" evoked response, i.e. the evoked response that would otherwise have occurred in response to just the V-pulse. Typically, the magnitude of the measured evoked response due to fusion is less than the true evoked response. In any case, the measure evoked response cannot be reliably used for the purposes of tracking heart failure or, typically, for any other purpose.

Although not shown in the figures, little evoked response can arise if a conducted P-wave/A-pulse reaches the ventricles before the V-pulse is applied. In such a circumstance, the ventricles begin to contract in response to the conducted P-wave/A-pulse before the V-pulse is delivered. As a result, the ventricles are refractory when the V-pulse is applied, i.e. the ventricles are not capable of responding to the V-pulse. Hence, the V-pulse does not trigger an evoked response and so no evoked response is measured. Note that the electrical signals associated with an intrinsic depolarization of the ventricles (which are referred to as the QRS complex) triggered by a conducted P-wave/A-pulse differ from the electrical signals associated with evoked response triggered by a V-pulse. Techniques for tracking heart failure based on changes in evoked response require an accurate measurement of the true evoked response.

To solve problems due to fusion, state-of-the-art pacemakers are programmed to reduce the AV/PV delay during measurement of the evoked response profile as shown in FIG. 3, which illustrates an A-IEGM 24 and a corresponding V-IEGM 26 during normal sinus rhythm. By reducing the delay, the conducted P-wave no longer fuses with the V-pulse and so the measured evoked response is due solely to the V-pulse and hence is properly representative of the true evoked response. Note that the conducted P-wave reaches the ventricles while the ventricles are refractory and hence have no effect on the resulting evoked response. Hence, the measured evoked response may be reliably used for the purposes of tracking heart failure or for other purposes. These and other techniques for avoiding fusion are discussed in, e.g., U.S. Pat. No. 5,334,220 to Sholder, entitled "Dual-Chamber Implantable Pacemaker Having an Adaptive AV Interval That Prevents Ventricular Fusion Beats and Method of Operating Same."

Although the solution of FIG. 3 is effective during normal sinus rhythm, fusion problems can still arise during atrial fibrillation (AF). This is illustrated in FIG. 4, which shows an A-IEGM 28 and a corresponding V-IEGM 30 during an episode of AF. During AF, the atria beat rapidly and erratically and so P-waves likewise occur rapidly and erratically. Hence, during AF, conducted P waves to ventricles are irregular and cannot be reliably tracked. So devices typically switch from a tracking mode (such as a VDD or DDD) to a nontracking mode (such as VVI or DDI), i.e. an asynchronous mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Accordingly, existing methods for determining the appropriate AV/PV delay are not applicable during AF. So the measured evoked response during AF in asynchronous (non-tracking) mode may be unpredictable due to possible fusion (or due pacing while the ventricles are refractory), thus preventing the evoked response from being used for tracking heart failure or for any other purpose requiring accurate detection of the true evoked response. Moreover, should a conducted P-wave/A-pulse reach the ventricles before the delivery of a V-pulse (and while the ventricles are non-refractory), the P-wave/A-pulse will trigger an intrinsic depolarization rendering the subsequent V-pulse ineffective and preventing the measurement of an evoked response.

As a result of the fusion problems shown in FIG. 4, current state-of-the-art pacemakers typically deactivate evoked response detection during AF. However, evoked response data obtained during AF is useful to aid in tracking heart failure and is potentially useful for other purposes as well. Hence, the inability to track evoked response during AF prevents the gathering of useful evoked response data. Indeed, within chronic AF patients, the inability to detect ventricular evoked response during AF results in a significant reduction in the amount of evoked response data that can be obtained, thus rendering any heart failure diagnosis based on evoked response less reliable. Chronic AF patients may be more vulnerable to the progression of heart failure than patients with normal sinus rhythm and so for chronic AF patients it would instead be desirable to obtain a greater amount of evoked response data rather than a lesser amount.

Accordingly, it would be highly desirable to provide techniques for reliably detecting ventricular evoked response profiles during AF and it is to that end that the invention is primarily directed. Other aspects of invention are directed to evaluating and tracking heart failure based on evoked response profile measurements obtained using the new detection techniques.

SUMMARY

In accordance with one embodiment, techniques are provided for measuring ventricular evoked response within the heart of a patient via an implantable medical device. Briefly, the device senses an intrinsic ventricular depolarization within one ventricular chamber then delivers a pacing pulse to the other ventricular chamber prior to intrinsic depolarization thereof. The evoked response generated in that chamber in response to the pacing pulse is then measured. For patients with a longer conduction delay to the right ventricle than to left ventricle, the intrinsic ventricular depolarization is sensed in the right ventricle and the pacing pulse is then promptly applied in the left ventricle. By delivering a pacing pulse to the left ventricle promptly upon detection of an intrinsic depolarization of the right ventricle, the pacing pulse is thereby applied before intrinsic depolarization of the left ventricle can commence. In this regard, for patients with a longer conduction delay from the atria to the right ventricle, the intrinsic depolarization of the right ventricle is triggered by a P-wave/A-pulse conducted from the atria. The P-wave/A-pulse is then conducted from the right ventricle to the left ventricle where, in the absence of a prior pacing pulse, it would trigger an intrinsic depolarization of the left ventricle. However, by delivering a pacing pulse to the left ventricle promptly following detection of the depolarization of the right ventricle, the left ventricular pacing pulse is thereby applied before the P-wave/A-pulse has time to propagate into the left ventricle. Hence, the left ventricle contracts solely in response to the ventricular pacing pulse and possible fusion between the pacing pulse and the conducted P-wave/A-pulse is avoided, permitting reliable detection of evoked response within the left ventricle.

It should be noted that the ventricular evoked response profile detected using this technique is a single chamber evoked response. Also, note that within any patients having a conduction pathway whereby the conducted P-wave/A-pulse reaches the left ventricle prior to the right ventricle, the implanted device is instead configured to sense an intrinsic depolarization in the left ventricle then promptly deliver a pacing pulse to the right ventricle for measuring evoked response in the right ventricle.

The invention is advantageously exploited to allow measurement of an evoked response profile during AF because it avoids possible fusion with conducted P-waves/A-pulses. However, the techniques of the invention may also be employed during normal sinus rhythm. Indeed, the use of the invention during sinus rhythm as well as during AF allows the device to employ a single evoked response measurement technique, thus eliminating any need for two separate evoked response measurement techniques (i.e. one technique for sinus rhythm and a different technique for AF.) Moreover, by using the technique the invention to measure single chamber evoked response during either sinus rhythm and AF, a comparison of sinus rhythm evoked response profiles and AF evoked response profiles may be more easily performed than if the sinus rhythm evoked response were a dual chamber evoked response whereas the AF evoked response were a single chamber evoked response.

Heart failure may then be tracked based on changes, if any, occurring over time in selected features of the measured evoked response profile. In particular, changes in the amplitude and slope of the evoked response may be quantified and tracked for the purposes of detecting the onset of heart failure and for tracking its progression or regression. Upon detection of heart failure or any significant progression thereof, appropriate warning signals are generated by the implanted device. In this manner, the patient is immediately alerted to any potentially life-threatening progression in heart failure so that immediate medical attention can be sought. The warning signals may be delivered directly to the patient using an implanted warning device, if provided, such as a vibrational warning device or a "tickle voltage" warning device. Additionally or alternatively, warning signals may be transmitted to a bedside warning device for display thereon and for forwarding to a physician. Therapy provided by the implanted device may be initiated or adjusted in response to detection or progression of heart failure. For example, upon detection of the onset of heart failure, CRT may be activated, assuming it is not already being performed. If an implantable drug pump is provided, appropriate medications may be automatically delivered to address heart failure. Diagnostic information representative of the severity and progression of heart failure is also stored for subsequent review by the physician.

Thus, various techniques are provided for use with implantable medical device for measuring evoked response during AF, detecting and tracking heart failure based on changes in evoked response, and for generating warning signals and delivering appropriate therapy, as needed. Other aspects, features and advantages of the invention will be apparent from the descriptions that follow.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Heart Failure-Responsive System

Figure 5:
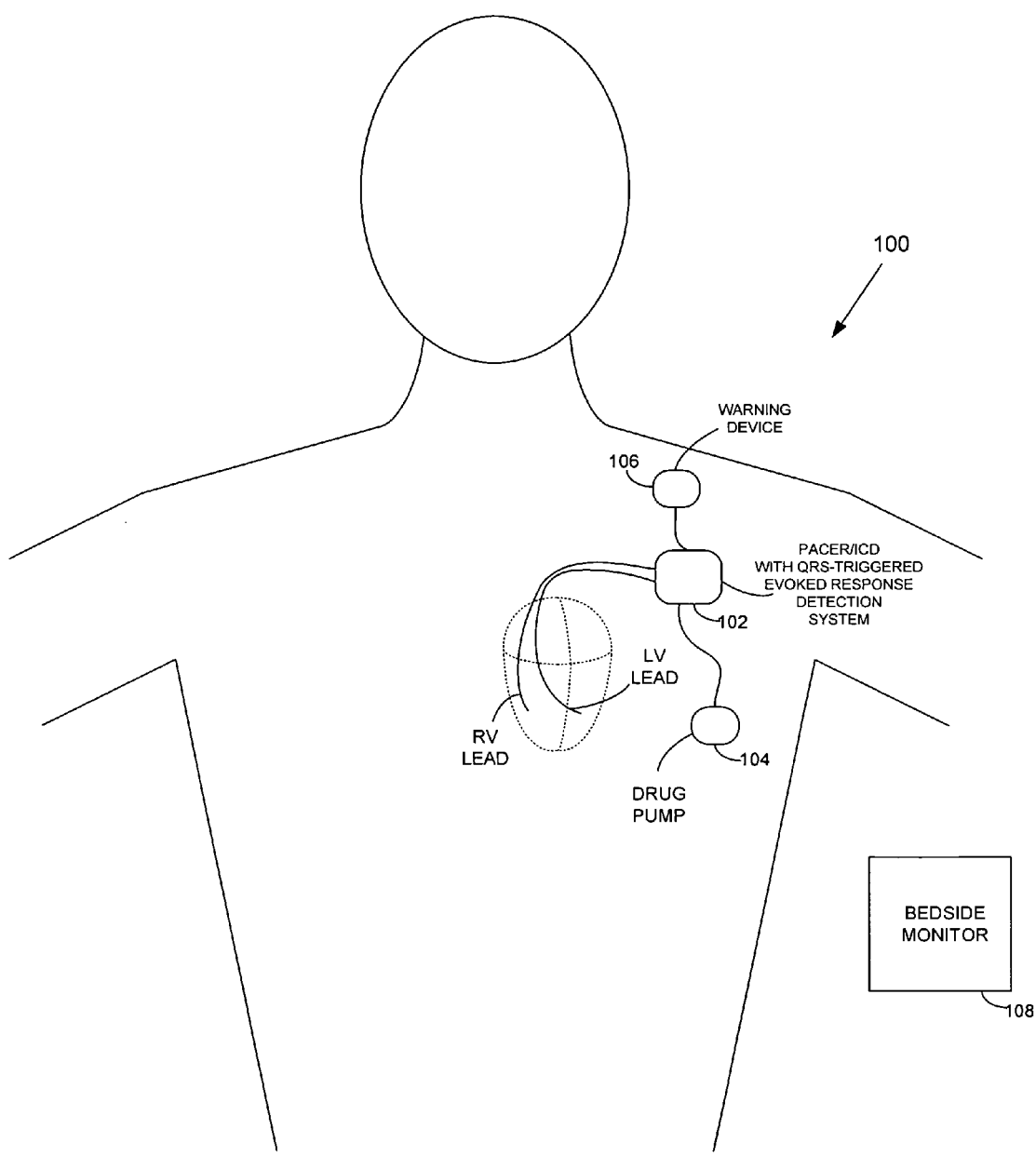
FIG. 5 illustrates pertinent components of an implantable heart failure-responsive medical system having a pacemaker or ICD capable of detecting ventricular evoked response during AF and further capable of detecting and evaluating heart failure based on ventricular evoked response.

FIG. 5 illustrates an implantable heart failure-responsive medical system 100 capable of (1) measuring evoked response during sinus rhythm or during AF; (2) detecting heart failure based on changes in evoked response; (3) evaluating its severity; (4) tracking its progression; and (5) delivering appropriate warnings and therapy. Heart failure-responsive system 100 includes a pacer/ICD 102 or other cardiac stimulation device that incorporates internal components for controlling evoked response detection and heart failure evaluation functions (shown individually in FIG. 12). To detect evoked response during AF, pacer/ICD 102 senses a QRS complex in the right ventricle (RV) using an RV lead and then immediately applies a V-pulse to the left ventricle (LV) using an LV lead, so as to avoid possible fusion involving conducted beats from the atria. A single chamber LV evoked response profile is then measured based on electrical signals sensed using the LV and RV leads. (In FIG. 5, simplified RV and LV pacing leads are shown. A full set of pacing leads and their electrodes are set forth in FIG. 11.) With this QRS-triggered technique, LV evoked response may be reliably detected even during AF. Otherwise conventional evoked response detection techniques may be employed during sinus rhythm. Alternatively, the QRS-triggered technique may be employed both during sinus rhythm as well as during AF. These techniques are described in greater detail below with reference to FIGS. 6-9.

Evoked response is periodically detected and selected features of the evoked response profile are then analyzed to detect the onset of heart failure so that appropriate therapy and warnings can be provided. The pacer/ICD then also evaluates the severity of the detected heart failure to, for example, identify the particular NYHA class of heart failure and to track the progression of heart failure based on any changes over time occurring in the evoked response profile. This is also described in greater detail below with reference to FIGS. 6-9. If heart failure is detected, then appropriate therapy is automatically delivered by pacer/ICD. For example, once heart failure has been detected, CRT therapy may be applied using the leads implanted in the ventricles in an attempt to improve cardiac function. Control parameters for CRT therapy are automatically adjusted based on the severity of the heart failure. Additionally, or in the alternative, the implantable heart failure-responsive system may be equipped with a drug pump 104 capable of the delivering drug therapy in an attempt to address heart failure. Discussions of possible medications for use in heart failure patients are provided below. Drug dosages provided by an implantable drug pump may be titrated based on the severity of heart failure.

If the onset of heart failure is detected or if a significant progression in heart failure is detected, warning signals are generated using either an internal warning device 106 or an external bedside heart failure monitor 108 to warn the patient. The internal warning device may be a vibrating device or a "tickle" voltage device that, in either case, provides perceptible stimulation to the patient to alert the patient of any significant progression of heart failure so that the patient may consult a physician. The bedside monitor may provide audible or visual alarm signals to alert the patient as well as textual or graphic displays. In addition, once heart failure has been detected, diagnostic information is stored within the pacer/ICD for subsequent transmission to an external programmer (not shown in FIG. 5) review by a physician or other medial professional. The physician may then prescribe any other appropriate therapies to address the heart failure. The physician may also adjust the operation of the pacer/ICD to activate, deactivate or otherwise control any therapies that are automatically applied. In addition, the bedside monitor may be directly networked with a centralized computing system for immediately notifying the physician of a significant increase in heart failure severity.

Hence, FIG. 5 provides an overview of an implantable system for measuring evoked response even during AF, detecting heart failure based on evoked response, evaluating its severity, tracking its progression and delivering appropriate therapy or warning signals. Embodiments may be implemented that do not necessarily perform all of these functions. Rather, embodiments may be implemented that provide, for example, only for measuring evoked response using the techniques of the invention but not for detecting or tracking heart failure based on evoked response. Moreover, systems provided in accordance with the invention need not include all the components shown in FIG. 5. In many cases, for example, the system will include only the pacer/ICD and its leads with heart failure therapy provided in the form of CRT. Drug pumps and warning devices are not necessarily implanted. Other implementations may employ an external monitor for generating warning signals but include no internal warning device. These are just a few exemplary embodiments. No attempt is made herein to describe all possible combinations of components that may be provided in accordance with the general principles of the invention. Also, note that, internal signal transmission lines provided for interconnecting the various implanted components are not shown in FIG. 5. Wireless signal transmission may alternatively be employed, such as wireless transmission employing so-called "BlueTooth" techniques. (BlueTooth is a registered trademark.) In addition, the particular locations of the implanted components shown in FIG. 5 are merely illustrative and may not necessarily correspond to actual implant locations.

Overview of QRS-Triqgered Detection of Evoked Response

Figure 6:
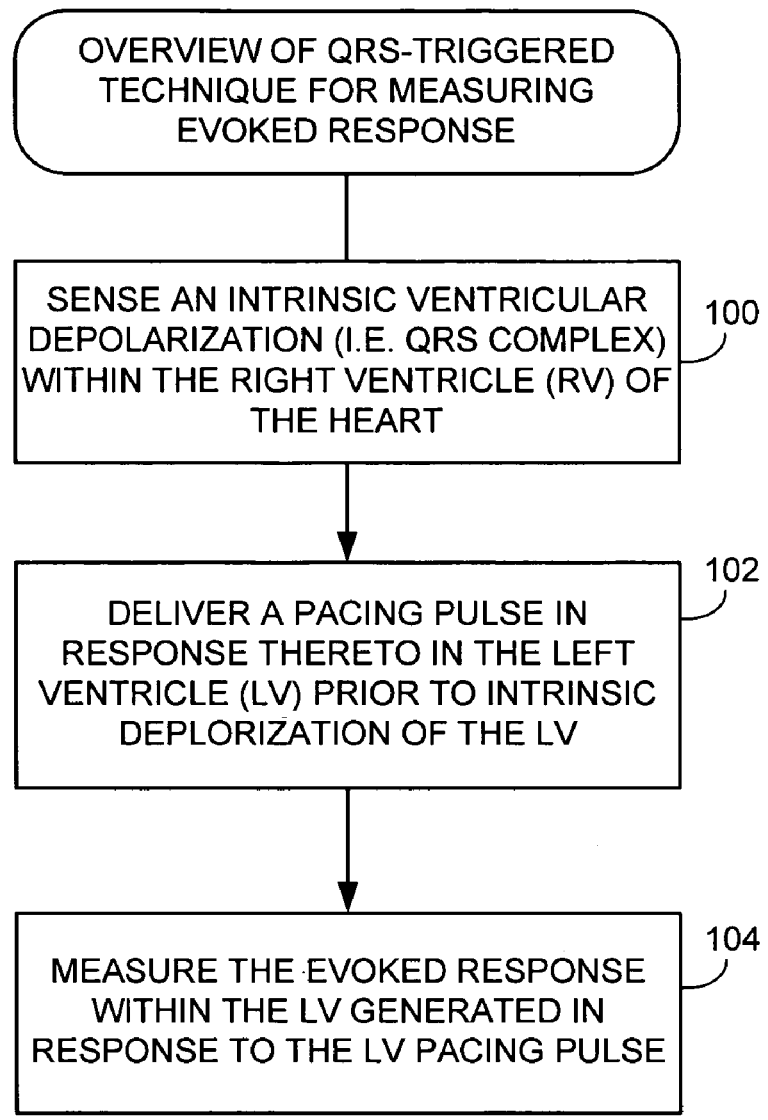
FIG. 6 is a flow diagram providing an overview of a QRS-triggered evoked response technique of the invention, which may be performed by the system of FIG. 5.

FIG. 6 provides an overview of the QRS-triggered evoked response measurement techniques of invention. The techniques of FIG. 6 are intended for use with patients with generally normal conduction pathways wherein P-waves/A-pulses conducted from the atria first reach the right ventricle and then the left ventricle, such that RV intrinsic depolarizations occur prior to LV intrinsic depolarizations. The techniques, however, are easily adapted for use with patients with alternate conduction pathways wherein P-waves/A-pulses conducted from atria first reach the left ventricle and then the right ventricle. For patients with normal conduction pathways, at step 100, the pacer/ICD senses an intrinsic ventricular depolarization (i.e. a QRS complex) within the right ventricle using the lead implanted in the right ventricle. Otherwise conventional techniques may be employed for detecting onset of the QRS complex. A pacing pulse is then delivered, at step 102, to the left ventricle using a lead implanted in the left ventricle and, at step 104, the evoked response within the LV is measured, i.e. a single chamber evoked response profile is measured. Otherwise conventional techniques may be employed for measuring the evoked response. See, for example, U.S. Pat. No. 5,697,957 to Noren, et al., entitled "Adaptive Method and Apparatus for Extracting an Evoked Response Component from a Sensed Cardiac Signal by Suppressing Electrode Polarization Components."

Figure 7:
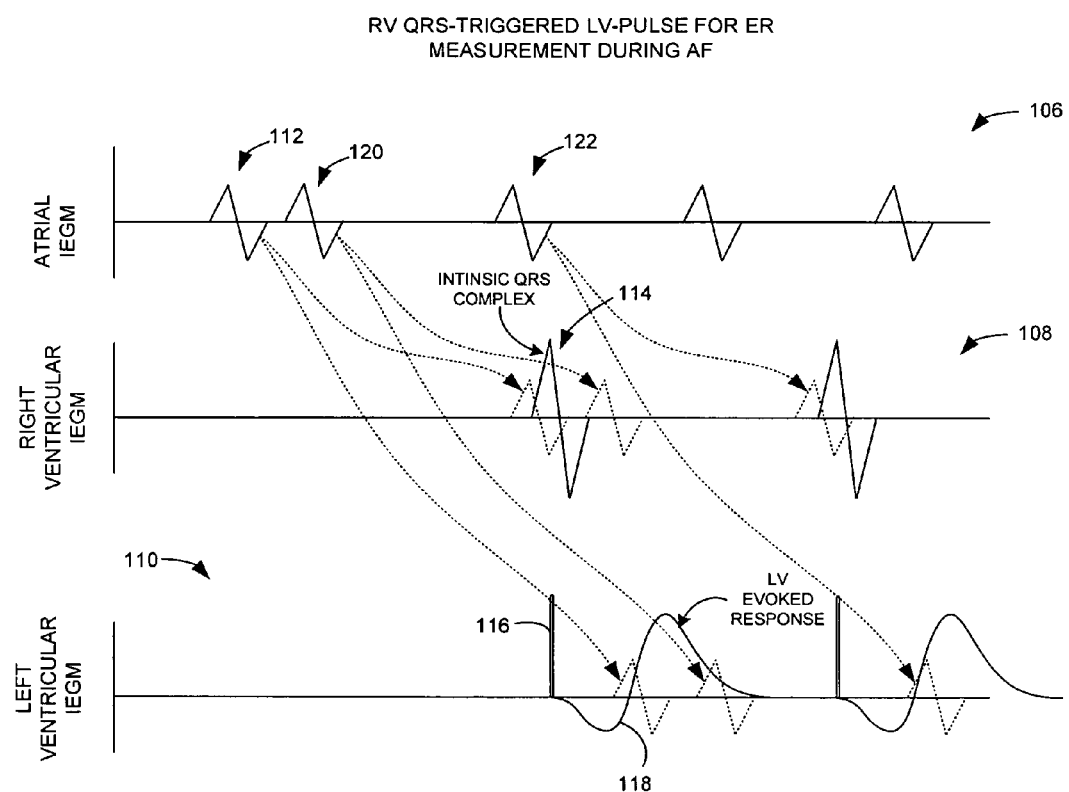
FIG. 7 is a stylized timing diagram illustrating atrial, RV, and LV IEGM signals processed by the technique of FIG. 6.

The LV-pacing pulse is delivered prior to possible intrinsic depolarization of the LV caused by conduction of electrical signals from the RV to the LV via the normal conduction pathways. In this manner, it is assured that the LV depolarizes in response to the LV pacing pulse and not in response to intrinsic electrical signals, thus allowing the true evoked response profile to be measured. This is illustrated in FIG. 7, which provides a stylized representations of an A-IEGM 106, an RV-IEGM 108, and an LV IEGM 110 for example where the heart is subject to AF. Within the A-IEGM, various erratic P-waves appear. Phantom lines illustrate the conduction of P-waves first to the right ventricle and then to the left ventricle. The conduction of a first P-wave 112 to the right ventricle triggers depolarization of the right ventricle, as manifest by QRS complex 114. Upon detection of the RV QRS complex, the pacer/ICD promptly delivers a pacing pulse 116 to the left ventricle, which triggers an evoked response 118 that is measured by the system. The LV-pulse is delivered to the left ventricle prior to conduction of P-wave 112 into the left ventricle and hence the left ventricle contracts in response to the pacing pulse rather than in response to be conducted P-wave. Instead, the P-wave reaches the left ventricle while the left ventricle is refractory and thus has no effect on the left ventricle. In the example of FIG. 7, a second P-wave 120 within the atria reaches the right and left ventricles while the ventricles are both refractory and hence has no effect. Eventually, a third P-wave 122 reaches the right ventricle when it is no longer refractory, thus producing another RV QRS, which triggers the delivery of another LV pacing pulse enabling measurement of another evoked response.

In one example, the LV pacing pulse is delivered substantially immediately upon sensing of the RV QRS-complex. However, it is sufficient that the LV pulse be delivered prior to the initiation of intrinsic depolarization of the left ventricle. Typically, it is sufficient that the LV pacing pulse be delivered within 20 milliseconds (ms) following detection of the RV QRS complex. For at least some patients, it may be desirable to provide for a slight RV-LV delay to improve cardiac function and so the pacer/ICD may be programmed to deliver the LV pulse subject to a specified time delay following detection of the RV QRS complex (so long as the LV pulse is still delivered prior to the initiation of intrinsic depolarization of the left ventricle.) Routine testing may be performed by a physician or other medical professional following implant of the pacer/ICD in the patient to set the timing by which the LV pulse is delivered. Routine testing may also be employed to verify that the patient has normal conduction pathways, i.e. that the intrinsic depolarization of the RV occurs prior to that of the LV. If the LV instead depolarizes prior to the RV, then the pacer/ICD is programmed to sense the LV QRS complex then deliver an RV pacing pulse.

Hence, with the technique of FIG. 6, even during AF, an evoked response profile may nevertheless be reliably measured. As will be explained below, the technique also may be employed during normal sinus rhythm. In either case, the resulting evoked response profile is a single chamber evoked response representative only of the evoked response within the left ventricle. Nevertheless, the single chamber evoked response profile is useful for evaluating heart failure within the patient and for many other applications where evoked response measurement is needed, such as verifying capture or the like.

Figure 8:
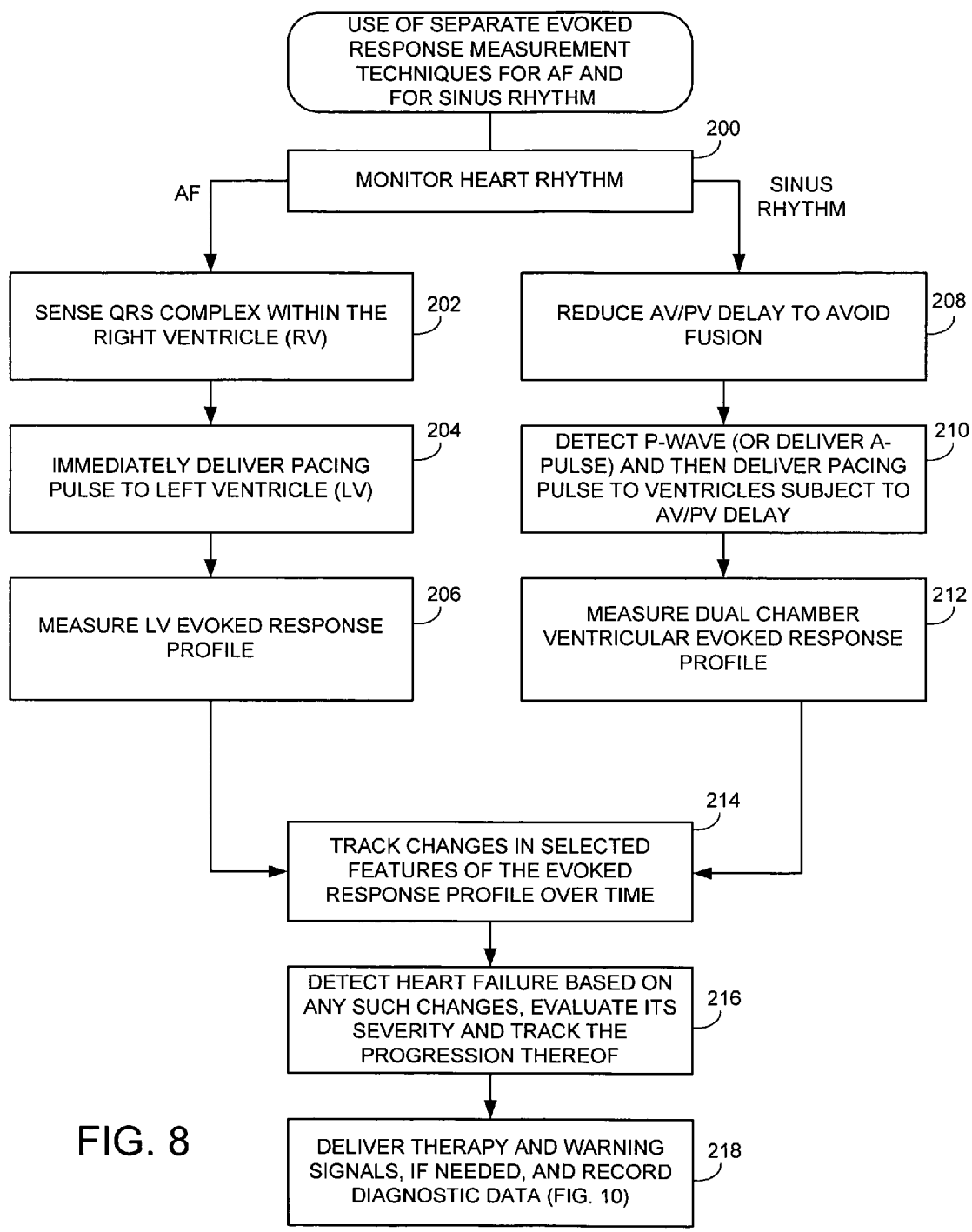
FIG. 8 is a flow diagram illustrating a first exemplary technique for detecting ventricular evoked response and for tracking heart failure based on ventricular evoked response, which exploits the general technique of FIG. 6, wherein different evoked response detection techniques are employed depending up whether the heart is in sinus rhythm or AF.
Figure 9:
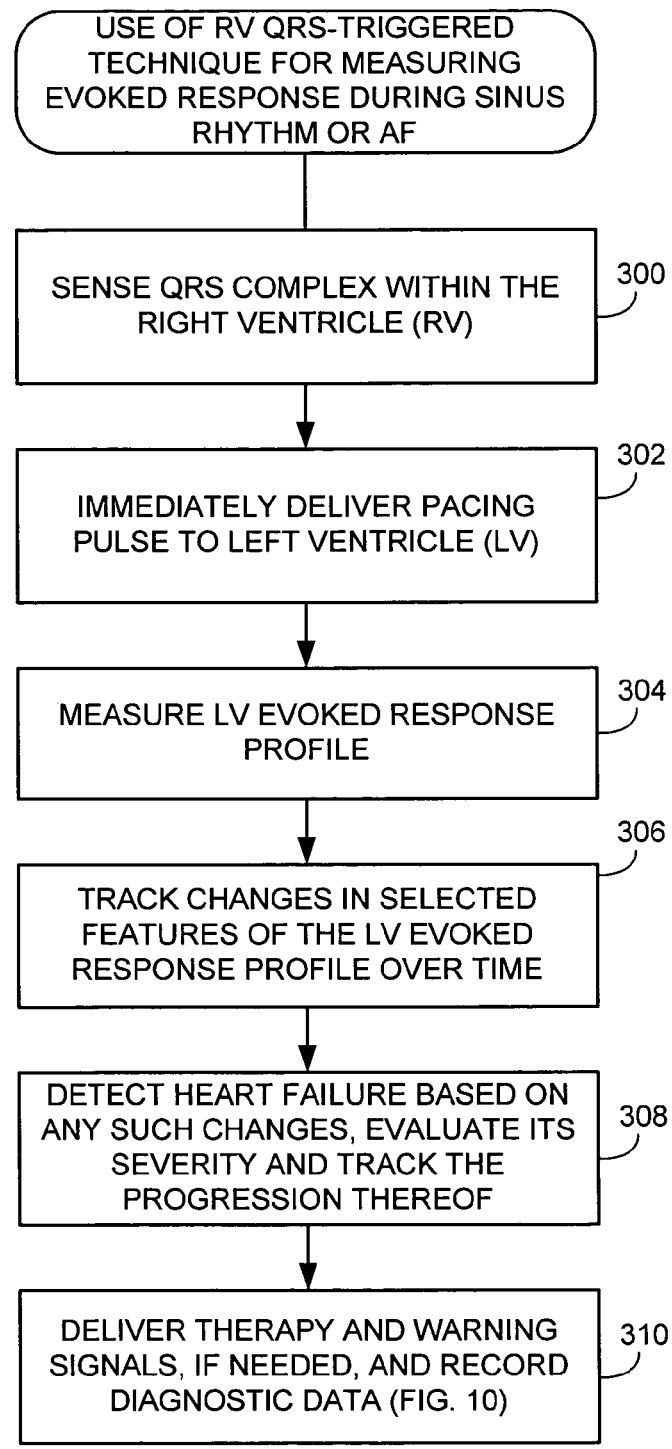
FIG. 9 is a flow diagram illustrating a second exemplary technique for detecting ventricular evoked response and for tracking heart failure, which also exploits the general technique of FIG. 6, but wherein a single evoked response detection technique is employed regardless of whether the heart is in sinus rhythm or AF.
Figure 10:
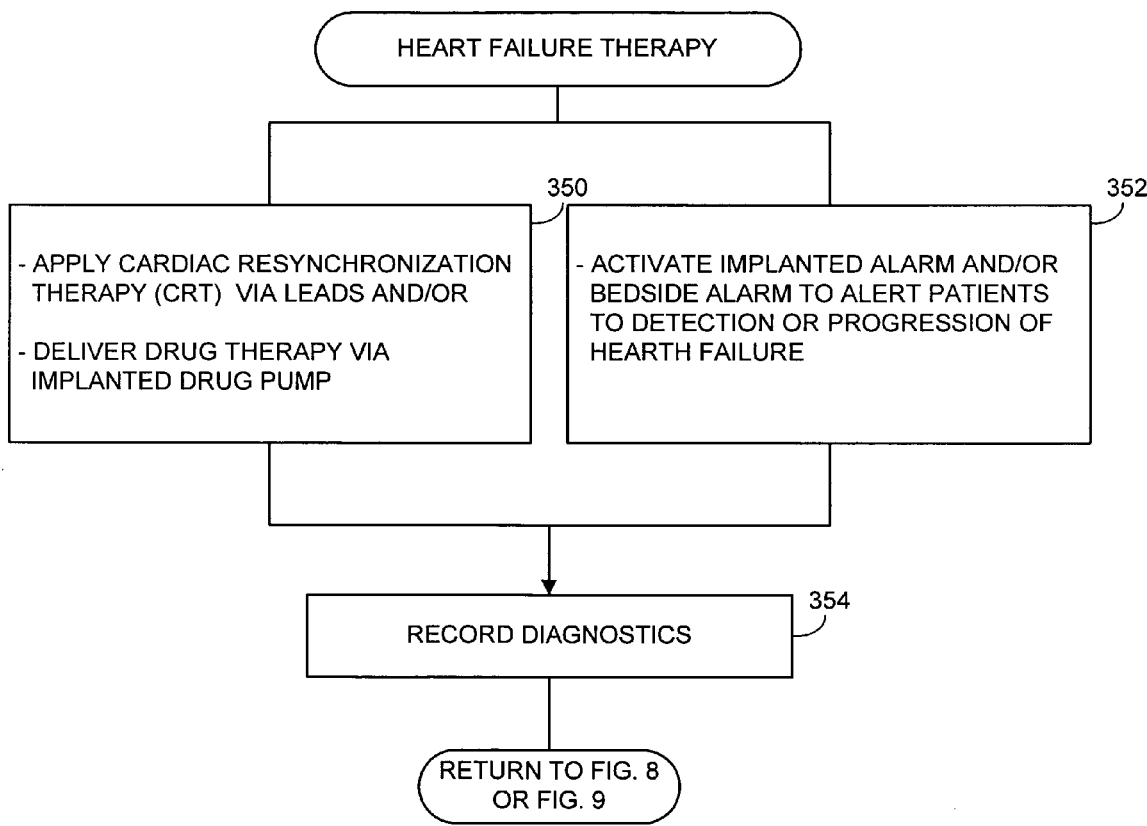
FIG. 10 is a flow diagram illustrating an exemplary method for use with the techniques of FIG. 8 or 9 for delivering therapy and warning signals in response to heart failure.

Turning now to FIGS. 8-10, various techniques for exploiting the QRS-triggered evoked response measurement technique of FIG. 6 will now be described.

Use of Separate AF and Sinus Rhythm Evoked Response Detection Techniques

Figure 2:
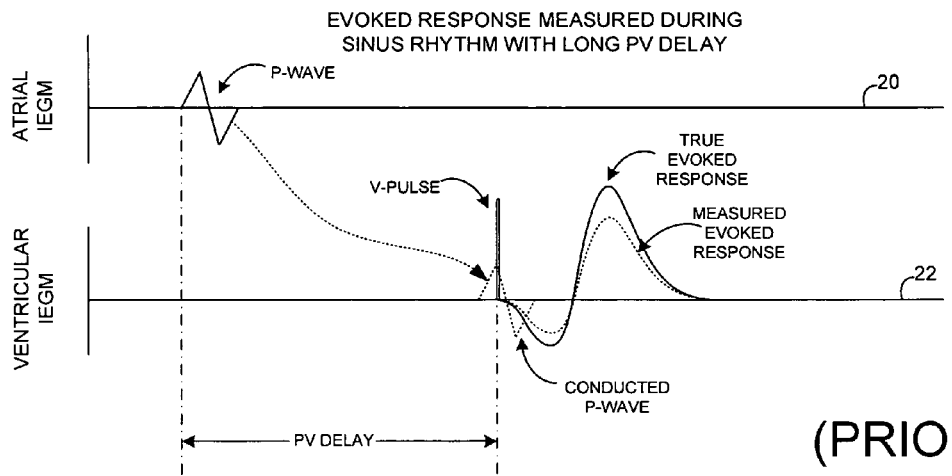
FIG. 2 is a stylized timing diagram illustrating fusion of a conducted P-wave and a ventricular pacing pulse during a normal sinus rhythm, which results in an inaccurate measurement of true ventricular evoked response.
Figure 3:
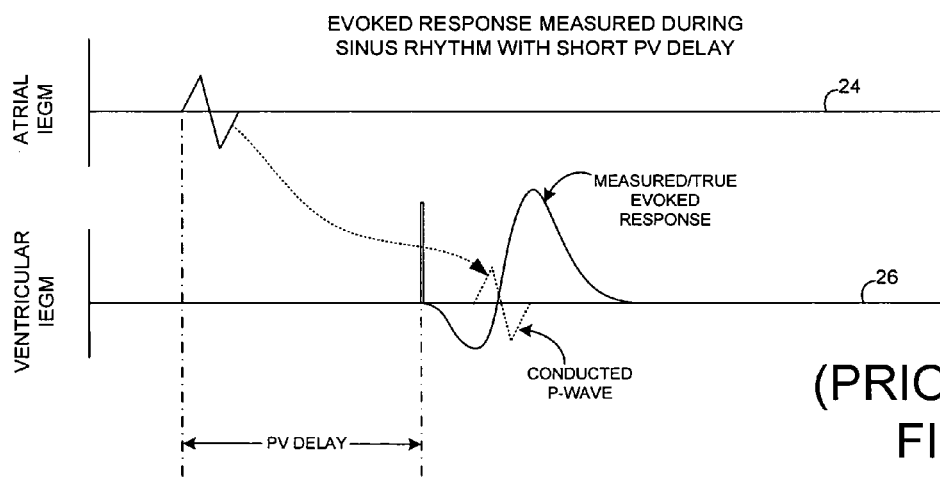
FIG. 3 is a stylized timing diagram illustrating a technique for avoiding fusion during normal sinus rhythm by reducing the PV delay.
Figure 4:
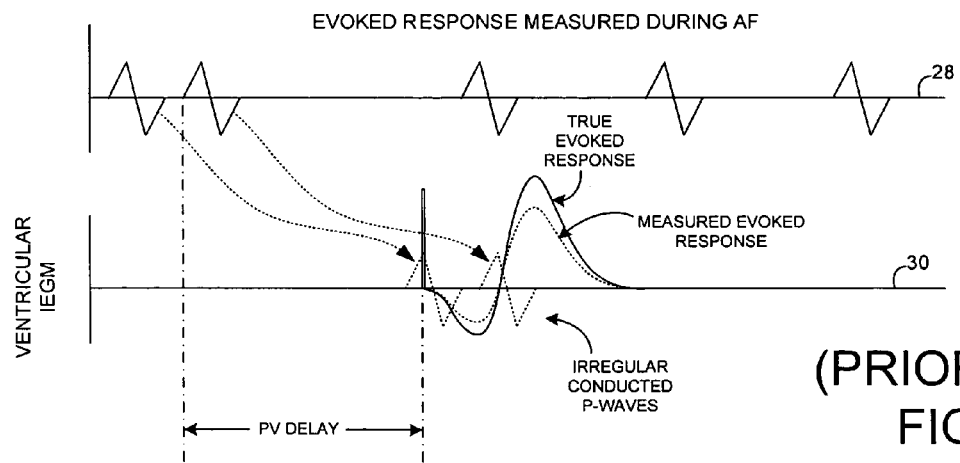
FIG. 4 is a stylized timing diagram illustrating fusion of a conducted P-wave and a ventricular pacing pulse during a AF, which again results in an inaccurate measurement of true ventricular evoked response.

FIG. 8 illustrates a technique wherein the QRS-triggered evoked response measurement techniques are used only during AF; otherwise conventional evoked response measurement techniques are used during sinus rhythm. Beginning at step 200, the pacer/ICD monitors the heart rhythm to detect the onset of AF. This may be performed in accordance with otherwise conventional techniques. Typically, the pacer/ICD is programmed to track the atrial rate and if it exceeds an AF detection threshold, AF is presumed. During AF, the above-described evoked response measurement techniques are employed to measure the LV evoked response profile, at steps 202-206. In addition, upon detection of AF, the pacer/ICD is preferably configured to perform AMS. However, if AF is not detected, then a dual chamber evoked response profile is instead detected, using steps 208-212. Briefly, at step 208, the pacer/ICD reduces a preprogrammed AV/PV pacing delay by an amount sufficient to avoid possible fusion of conducted P-waves/A-pulses from the atria (as described above in connection with FIGS. 2-3). At step 210, the pacer/ICD detects P-waves in the atria (or delivers A-pulses) and then delivers V-pulses to the ventricles subject to the reduced AV/PV delay, thus permitting measurement of the dual chamber evoked response profile, at step 212.

Then, beginning at step 214, the pacer/ICD tracks changes in selected features of the evoked response profiles over time. Since the evoked response measured during AF is a single chamber evoked response profile, whereas the evoked response measured during sinus rhythm is a dual chamber evoked response profile, the profiles are preferably stored and analyzed separately. At step 216, the onset of heart failure, if any, is detected based upon changes occurring within selected characteristics of the evoked response profile over time. Techniques for evaluating heart failure within a patient based upon evoked response are described in detail in the above-referenced patent to Bradley. Pertinent aspects of these techniques are summarized below as well. In addition, at step 216, any progression or regression of heart failure is also tracked based upon those changes. Given that the evoked response profile measured during AF is a single chambered profile whereas the evoked response profile measured during sinus rhythm is a dual chamber profile, the pacer/ICD preferably evaluates the evoked response profiles separately for the purposes of detecting and tracking heart failure. In one example, the pacer/ICD calculates a numerical value representative of detection of the onset of heart failure based upon the single chambered values and also calculates a separate numerical value representative of detection of the onset of heart failure based upon the dual chambered values. The device then combines the values to yield a single value, which is used for heart failure detection and tracking purposes. Techniques for combining different parameters into a single value for evaluation are set forth in U.S. Patent Application 2004/0138716, of Koh et al., entitled "System and Method for Detecting Circadian States Using an Implantable Medical Device", published Jul. 15, 2004. Finally, at step 218, therapy and/or warning signals are generated, if needed, and a diagnostic data is recorded for subsequent review by a physician during a follow-up patient session with the patient. This is described more fully below in connection with FIG. 10.

Figure 1:
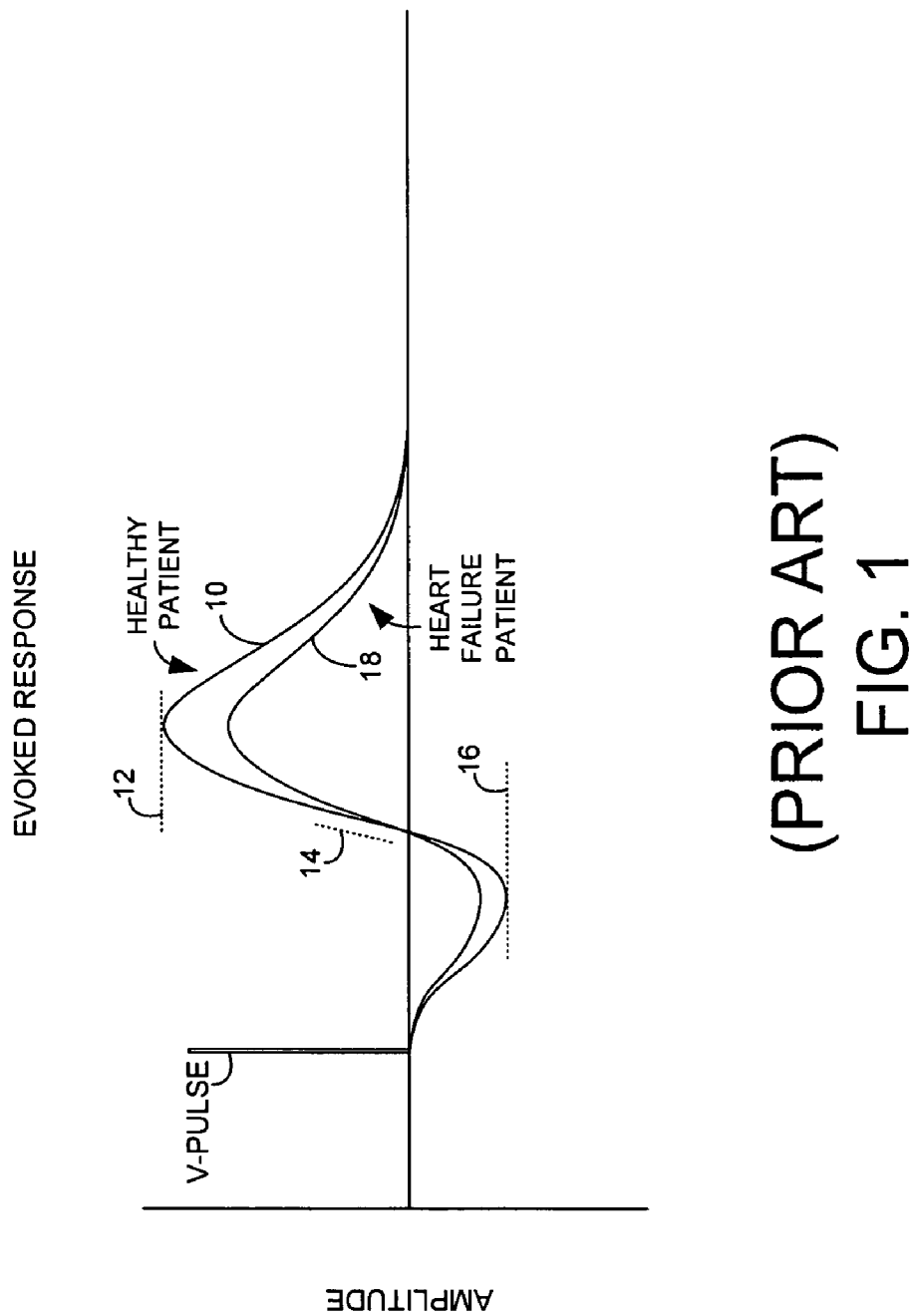
FIG. 1 is a stylized timing diagram illustrating ventricular evoked response.

As previously discussed, selected features of the evoked response profile are indicative of the onset and progression or regression of heart failure. The evoked response features, which may be quantified to this end relate to conduction velocity, fractionation, wall thickness, and heterogeneity of repolarization. Measurements of conduction velocity may be estimated from the positive slope of the evoked response, i.e. slope 14 of FIG. 1. If the evoked response is modeled as propagation of the depolarization wavefront away from the stimulation electrode, and the wavefront is modeled as a moving dipole, then the potential at the measurement electrode (ideally the pacing electrode) is inversely related to the conduction velocity of the myocardial tissue. If the conduction velocity is increased, the slope of the evoked response will increase and if the conduction velocity is decreased, the slope of the evoked response will decrease. Measurements of conduction velocity may be used to infer autonomic nervous system (ANS) tone as it affects the myocardium. Similarly, it may be used to assess the effectiveness of drug therapy administered by the physician.

With respect to fractionation, if the conduction away from the stimulation electrode is slowed through an area relative to other areas measured by the evoked response, then the evoked response will become fractionated. As fractionation occurs, the evoked response may appear discontinuous (more jagged) or less smooth. The degree of fractionation relates to the degree of continuity of the evoked response and may be quantified by template matching, feature characterization, or frequency information such as Fast Fourier Transform (FFT) spectra, all of which are well known in the art. Fractionation may result due to increased interstitial fibrosis, progressive necrosis from a recent myocardial infarction, or changes in cell geometry. Thus, measurement of such fractionation provides a measure of myocardial state.

Wall thickness estimates may be made from the maximum negative amplitude (amplitude 16 of FIG. 1) or the maximum positive amplitude (amplitude 12 of FIG. 1) of the evoked response. If the number of active cells (those capable of depolarizing and propagating a depolarization) are modeled as signal sources, then, as the wall thickness decreases due to changed filling or progressive dilation of the myocardium, there will be fewer cells within a few space constants or the "view" of the stimulation and sensing electrodes. With fewer such signal sources, the evoked response amplitude will be smaller since the sense electrode effectively integrates the action potentials within a few space constants of the sense electrode. Hence, as the wall thickness decreases, the evoked response amplitude will be smaller. This feature may be used for monitoring the progression of cardiac dilation in CHF, or to derive estimates of wall tension or diastolic stiffness, or even to optimize AV/PV delay.

Also, the amplitude of the evoked response is correlated to conduction velocity at the underlying cells. The intracellular resistivity of the myocardial cells is inversely related to the square of the conduction velocity. Since the transmembrane current is proportional to the spatial derivative of the intracellular current, then the transmembrane current is also proportional to the conduction velocity. Finally, the evoked response, being an extracellular potential, is therefore proportional to the conduction velocity by the integral of the transmembrane current over the volume of tissue beneath the electrode. Thus, increased conduction velocity will generate larger evoked responses. In this manner, the amplitude of the evoked response may be used as a surrogate for the myocardial state.

Furthermore, heterogeneity of repolarization measurements may be made using the maximum positive T-wave amplitude, the maximum negative T-wave amplitude, or the negative T-wave slope of the T-wave following a captured stimulation pulse. (The T-wave, which represents the repolarization of the ventricles, is not shown in the attached figures). Since the evoked response integrates the action potentials of the local cells, the homogeneity of the repolarization of these cells will be indicated by the amplitude and slew rate of the T-wave. For example, if all of the cells within the evoked response space constant repolarize in an organized fashion, both the T-wave amplitude and slope will be relatively large and smooth. However, if the cells repolarize in a more chaotic manner, the amplitude and slope of the T-wave may be reduced and/or fractionated. Such changes in amplitude and slope may be used to estimate the predisposition of the heart to arrhythmia to enable the physician to titrate anti-arrhythmic drugs and/or pacing therapy or to determine the appropriate device response to a sensed premature ventricular contraction or to ready an ICD for shock delivery.

Thus, any or all of the these features of the evoked response may be numerically quantified and combined into a single metric value representative of heart failure within the patient. The single value is then compared against various threshold values representative of the onset of heart failure and/or representative of various degrees of severity of heart failure. Routine studies may be performed to specify various threshold values representative of a different degrees of severity of heart failure, such as those set forth in the NYHA classification scheme summarized above, so as to allow the pacer/ICD to classify the severity of heart failure, if any, within the patient. However, the pacer/ICD need not specifically relate the severity of heart failure with the NYHA classification scheme. Rather, the pacer/ICD may instead simply be programmed to classify heart failure as, for example, "mild", "intermediate", or "severe". As can be appreciated, a wide range of techniques may be employed for evaluating the severity of heart failure or other heart diseases and for quantifying that evaluation and no attempt is made herein to describe all such techniques.

Furthermore, the evaluation of heart failure based upon the analysis of evoked response may be combined with any other appropriate heart failure detection or evaluation technique. See, for example, U.S. patent application Ser. No. 10/810,437 of Min et al., filed Mar. 26, 2004, entitled "System and Method for Evaluating Heart Failure Based on Ventricular End-Diastolic Volume Using an Implantable Medical Device." See also, U.S. Pat. No. 6,645,153, to Kroll et al., entitled "System And Method For Evaluating Risk Of Mortality Due To Congestive Heart Failure Using Physiologic Sensors", which describes a technique for determining a CHF mortality risk metric based on a combination of estimated ventilatory response values and the slope of heart rate reserve as a function of predicted heart rates.

Thus, FIG. 8 illustrates a technique for evaluating heart failure based upon evoked response wherein QRS-triggered evoked response measurement techniques are used during AF, whereas otherwise conventional measurement techniques are used during normal sinus rhythm. In the following, an alternative technique is described wherein QRS-triggered evoked response measurement techniques are used for both AF and sinus rhythm.

Use of Single AF and Sinus Rhythm Evoked Response Detection Technique

FIG. 9 illustrates a technique for evaluating heart failure based on changes in selected features of evoked response profiles measured using the QRS-triggered technique, during either AF or sinus rhythm. Many of the steps of FIG. 9 are similar or identical to those of FIG. 8 and hence will not be described again in detail. Since the technique of FIG. 9 employs the single chamber QRS-triggered measurement technique at all times, it is not necessary for the pacer/ICD to monitor heart rhythm to detect AF for the purposes of selecting an evoked response measurement technique. Nevertheless, preferably, pacer/ICD still monitors heart rhythm for the purposes of mode switching. For clarity in illustrating pertinent features invention, the step of monitoring heart rhythm is not shown in FIG. 9. In any case, at steps 300-304, the pacer/ICD measures the LV evoked response profile using techniques already described. At step 306, the pacer/ICD tracks changes in selected features of the LV evoked response profile over time to permit detection and tracking of heart failure, at step 308. Therapy and appropriate warning signals, if needed, are generated step 310. Appropriate diagnostic data is also recorded.

Thus, with technique of FIG. 9, a single chamber LV evoked response profile is measured regardless of the mode of operation of the pacer/ICD, i.e. regardless of whether the device has detected AF or not. As a result, the pacer/ICD may more easily compare evoked response profiles sensed during sinus rhythm with those sensed during AF, thus eliminating any need to separately track and evaluate single chamber and dual chamber evoked response profiles, as with the technique of FIG. 8.

Summary of Heart Failure Therapy

Referring now to FIG. 10, heart failure therapy, activated at step 218 or FIG. 8 or step 310 of FIG. 9, will be summarized. At step 350, the pacer/ICD controls delivery of CRT and/or drug therapy to the patient. CRT and related therapies are discussed in the above-referenced patents to Mathis, et al., Kramer, et al., and Stahmann, et al. The degree of severity of heat failure may be used to control CRT pacing parameters such as the time delay between left and right ventricular pulses to, for example, provide more aggressive CRT for more severe heart failure. Drug therapy is delivered using an implanted drug pump, if one is provided. Exemplary heart failure medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure that are safe and effective for use in connection with an implantable drug pump. Dosages may be titrated based upon the severity of heart failure. Implantable drug pumps are discussed in U.S. Pat. No. 5,328,460 to Lord, et al., entitled "Implantable Medication Infusion Pump Comprising Self-Contained Acoustic Fault Detection Apparatus".

Simultaneously, at step 352, the pacer/ICD may activate the implanted warning device or the bedside monitor, or both, to alert the patient to the initial detection of heart failure or to any significant progression thereof. The aforementioned patent to Lord et al. also discusses implantable "tickle" warning devices. As noted above, the bedside monitor may be directly networked with a centralized computing system for immediately notifying the physician as well. A system incorporating bedside monitoring units connected to a centralized external programmer system is described in U.S. Pat. No. 6,622,045 to Snell et al., "System and Method for Remote Programming of Implantable Cardiac Stimulation Devices." At step 354, appropriate diagnostic information is stored within a memory of the pacer/ICD for subsequent transmission to external programmer during a follow-up session with the patient for review by a physician or for immediate transmission via the bedside monitor to the centralized computing system, if one is provided.

Thus, FIGS. 6-10 illustrate the evoked response detection techniques and the heart failure evaluation techniques of the invention. The techniques may be exploited within any appropriate implantable medical device. For the sake of completeness, an exemplary pacer/ICD will now be described.

Exemplary Pacer/ICD

Figure 11:
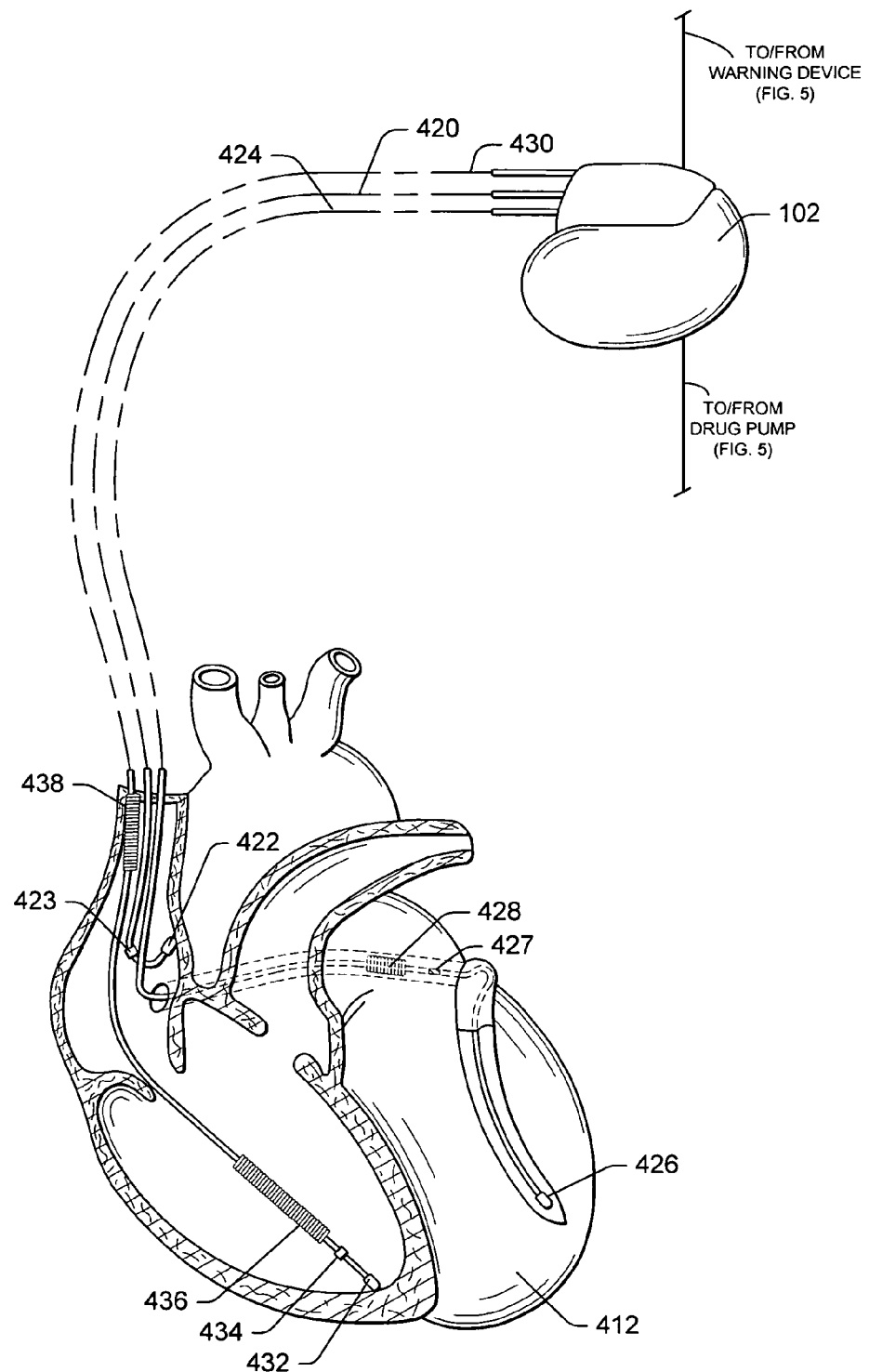
FIG. 11 is a simplified, partly cutaway view, illustrating the pacer/ICD of FIG. 5 along with a full set of leads implanted in the heart of the patient.

FIG. 11 provides a simplified block diagram of the pacer/ICD 102 of FIG. 5, which is a dual-chamber stimulation device capable of treating both fast and slow arrhythmias with stimulation therapy, comprising cardioversion, defibrillation, and pacing stimulation. To provide atrial chamber pacing stimulation and sensing, pacer/ICD 102 is shown in electrical communication with a heart 412 by way of a left atrial lead 420 having an atrial tip electrode 422 and an atrial ring electrode 423 implanted in the atrial appendage. Pacer/ICD 102 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle. RV tip electrode 432 is preferably used for sensing the QRS for QRS-triggered evoked response detection.

To sense left atrial and ventricular cardiac signals and to provide left chamber pacing therapy, pacer/ICD 102 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, comprising any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. LV tip electrode 426 is preferably used for delivering the responsive LV pacing pulse for use in QRS-triggered evoked response detection. Although only three leads are shown in FIG. 11, it should also be understood that additional stimulation leads (with one or more pacing, sensing and/or shocking electrodes) might be used in order to efficiently and effectively provide pacing stimulation to the left side of the heart or atrial cardioversion and/or defibrillation.

Figure 12:
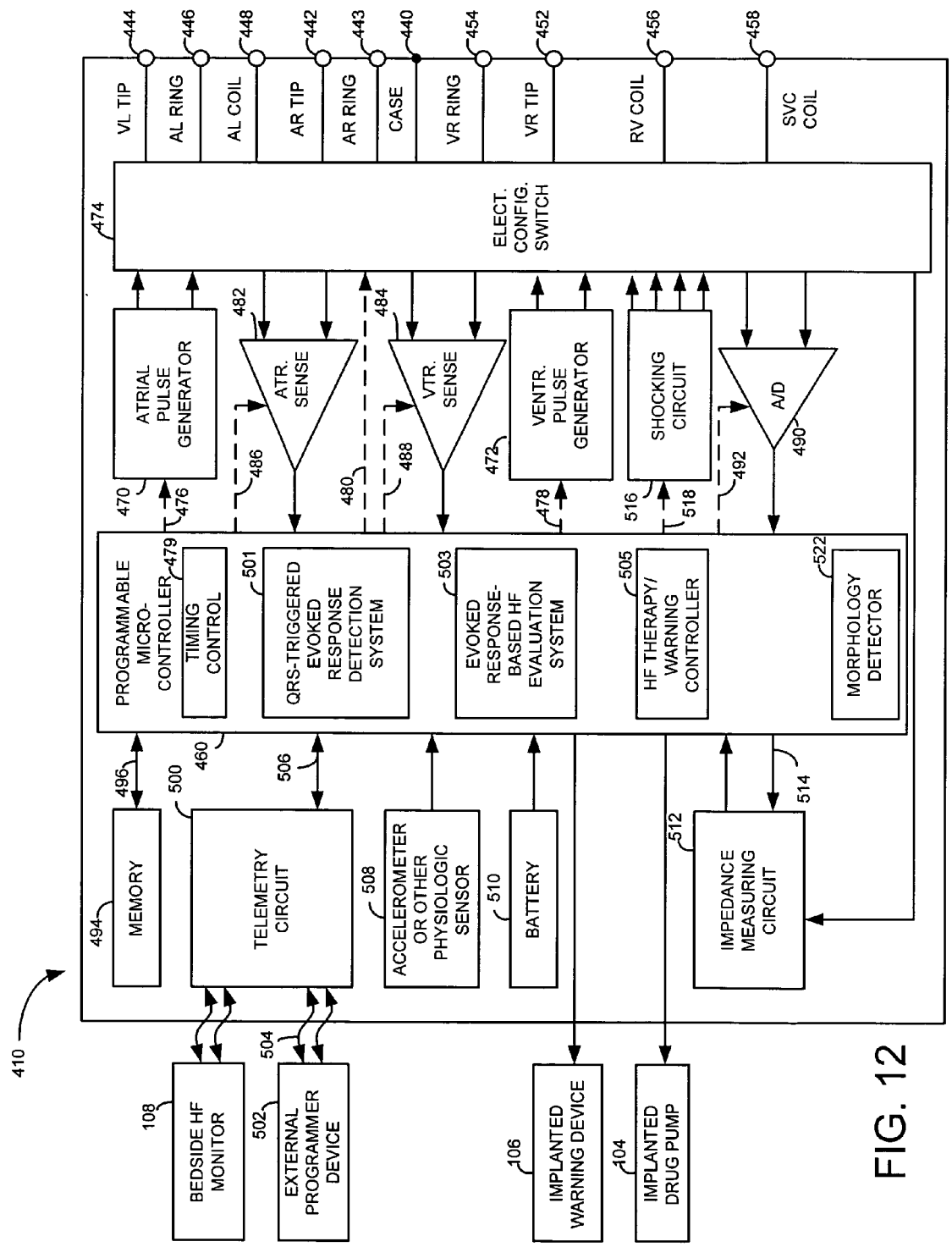
FIG. 12 is a functional block diagram of the pacer/ICD of FIG. 11, illustrating basic circuit elements that provide cardioversion, defibrillation and/or pacing stimulation in the heart and particularly illustrating components for measuring ventricular evoked response, tracking heart failure based on ventricular evoked response, and controlling delivery of therapy or warning signals in response thereto.

A simplified block diagram of internal components of pacer/ICD 102 is shown in FIG. 12. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 102, shown schematically in FIG. 12, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 102 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 12, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 used to control the timing of such stimulation pulses (e.g., pacing rate, atrio-ventricular (AV) delay, atrial interconduction (A-A) delay, or ventricular interconduction (RV-LV) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 102 to deal effectively with the potentially difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 102 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, AF, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 102 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 102 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 102 (as contained in the microcontroller 460 or memory 494) to be sent to the external device 502 through an established communication link 504. Pacer/ICD 102 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV/PV delay, RV-LV delay, etc.) at which the atrial and ventricular pulse generators, 470 and 472, generate stimulation pulses. While shown as being included within pacer/ICD 102, it is to be understood that the physiologic sensor 508 may also be external to pacer/ICD 102, yet still be implanted within or carried by the patient. A common type of rate responsive sensor is an activity sensor incorporating an accelerometer or a piezoelectric crystal, which is mounted within the housing 440 of pacer/ICD 102. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 12. The battery 510 may vary depending on the capabilities of pacer/ICD 102. If the system only provides low voltage therapy, a lithium iodine or lithium copper fluoride cell may be utilized. For pacer/ICD 102, which employs shocking therapy, the battery 510 must be capable of operating at low current drains for long periods, and then be capable of providing high-current pulses (for capacitor charging) when the patient requires a shock pulse. The battery 510 should also have a predictable discharge characteristic so that elective replacement time can be detected. Accordingly, pacer/ICD 102 is preferably capable of high voltage therapy and appropriate batteries are employed.

As further shown in FIG. 12, pacer/ICD 102 includes an impedance measuring circuit 512, which is enabled by the microcontroller 460 via a control signal 514. Impedance may be detected for use in tracking respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 512 is advantageously coupled to the switch 74 so that any desired electrode may be used.

In the case where pacer/ICD 102 is intended to operate as an implantable cardioverter/defibrillator (ICD) device, it detects the occurrence of an arrhythmia, and, if so programmed, automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Insofar as heart failure monitoring is concerned, the microcontroller includes a QRS-triggered evoked response detection system 501, which is operative to detect a single chamber evoked response profile using the techniques described above. An evoked response-based heart failure evaluation unit of 503 is operative to detect and evaluate heart failure, if any, within the patient based upon the evoked response profile, alone or in combination with other patient parameters that may also be indicative of heart failure. Finally, a heart failure therapy/warning controller 505 is also provided, which is operative to control the delivery of therapy and/or warning signals in response to detection of heart failure. In this regard, controller 505 sends appropriate control signals to implanted drug pump 104, implanted warning device 106 or external bedside monitor 108, as needed. Controller 505 also controls the recording of appropriate diagnostic data representative of changes in evoked response and representative of the detection and evaluation of heart failure within memory 494 for subsequent transmission to external programmer device 502 for review by a physician or other medical professional. Depending upon the implementation, the aforementioned components of the microcontroller may be configured as separate software or hardware modules. The modules may be combined to permit single modules to perform multiple functions.

What have been described are various systems and methods for use with a pacer/ICD. However, principles of the invention may be exploiting using other implantable systems or in accordance with other techniques. Thus, while the invention has been described with reference to particular exemplary embodiments, modifications can be made thereto without departing from the spirit and scope of the invention. Note also that the term "comprising" as used herein is intended to be inclusive, i.e. "comprising but not limited to."

What is claimed is:

1. A method for measuring evoked response within the heart of a patient via an implantable medical device, the method comprising:

sensing an intrinsic ventricular depolarization within a ventricular chamber of the heart;

delivering a pacing pulse in response thereto to the opposing ventricular chamber prior to intrinsic depolarization thereof;

detecting an evoked response generated in response to the pacing pulse;

tracking changes in the evoked response over time as a surrogate for a patient condition;

detecting atrial fibrillation (AF) and wherein sensing the intrinsic ventricular depolarization, delivering the pacing pulse in response thereto, and detecting the evoked response are only performed during AF.

2. The method of claim 1 wherein, if the heart is not subject to an ongoing AF, then performing the alternative steps of:

reducing an atrioventricular delay by an amount sufficient to avoid fusion between atrial depolarization signals conducted from the atria and ventricular pacing pulses;

delivering a ventricular pacing pulse; and measuring the evoked response generated in response to the pacing pulse.

* * * * *